US006579273B2

(12) United States Patent
Dupuy

(10) Patent No.: US 6,579,273 B2
(45) Date of Patent: Jun. 17, 2003

(54) REUSABLE BABY DIAPER HAVING REUSABLE ABSORBENT INSERT

(76) Inventor: Tereson R. Dupuy, 128 Alameda St., New Iberia, LA (US) 70563

( * ) Notice: Subject to any disclaimer, the term of this patent is extended or adjusted under 35 U.S.C. 154(b) by 0 days.

(21) Appl. No.: 09/903,829

(22) Filed: Jul. 11, 2001

(65) Prior Publication Data
US 2002/0010452 A1 Jan. 24, 2002

Related U.S. Application Data
(60) Provisional application No. 60/218,785, filed on Jul. 18, 2000.

(51) Int. Cl.$^7$ ................................................. A61F 13/15
(52) U.S. Cl. .................... 604/385.14; 604/395; 604/402
(58) Field of Search .......................... 604/386–7, 393–5, 604/397–402, 385.14, 385.21–385.22

(56) References Cited

U.S. PATENT DOCUMENTS

| | | | | | |
|---|---|---|---|---|---|
| 3,693,621 A | * | 9/1972 | Jarusik et al. | ......... | 210/321.89 |
| 4,548,604 A | * | 10/1985 | Ellsworth | .............. | 604/385.24 |
| 5,019,068 A | * | 5/1991 | Perez et al. | .................. | 604/386 |
| 5,451,219 A | * | 9/1995 | Suzuki et al. | ................ | 604/358 |
| 5,814,037 A | * | 9/1998 | Coates | .................. | 604/385.15 |
| 6,406,469 B1 | * | 6/2002 | Brain et al. | .................. | 604/394 |

OTHER PUBLICATIONS

"Fuzzi Bunz" web page by Tereson Dupuy www.fuzzibunz.com/fuzzi.html Downloaded Mar. 6, 2001.
"Fuzzi Bunz Lites" by Tereson Dupuy web page www.fuzzibunz.com/lites.html Downloaded Mar. 6, 2001.
"Heavenly Hineys" web page Downloaded Mar. 6, 2001 www.worldshopping.com/mall/heavenly/aio.html.
"Heavenly Hineys Diapers" Downloaded Mar. 6, 2001 www.worldshopping.com/mall/heavenly/diapers.html.
"Heavenly Hineys All In Ones" Downloaded Jul. 10, 2001 www.heavenlyhineys.com/products.html.
Erika Froese "What Goes into Making a Good Cloth Diaper", Baby Shop Magazine, Fall/Winter 1998 Mother ease web site, www.motherease.com/infoE.html.
Alexander Essentials web page "Daisy Diapers" www.daisydiapers.com/ ,Copyright 1999.2000 G.B.
"Loving Comfort" web page, Baby Products www.lovingcomfort.com/babyprod.htm Mar. 22, 2001.

* cited by examiner

Primary Examiner—Weilun Lo
Assistant Examiner—C. Lynne Anderson
(74) Attorney, Agent, or Firm—Jones, Walker, Waechter, Poitevent, Carrere & Denegre, L.L.P.

(57) ABSTRACT

An adjustable, form fitted, reusable diaper for infants that includes a reusable or disposable pad insertable between a soft permeable inner panel and an impermeable outer panel laminated with either a soft pile or a waterproof breathable or non-breathable elastomeric non-woven material. The diaper, having an hourglass configuration when open, is provided with expandable leg openings and waistband and fitted with hidden snap closures uniquely arranged to provide waist adjustment independently of leg opening adjustment and vise-versa. The diaper's use of a high pile, permeable inner panel such as polar fleece wicks moisture quickly away from the infants body where it is absorbed by the washable, reusable pad located between the inner and outer panels. The pad is then easily removed and replaced with a clean and dry pad, often without removal of the diaper from the infant.

13 Claims, 2 Drawing Sheets

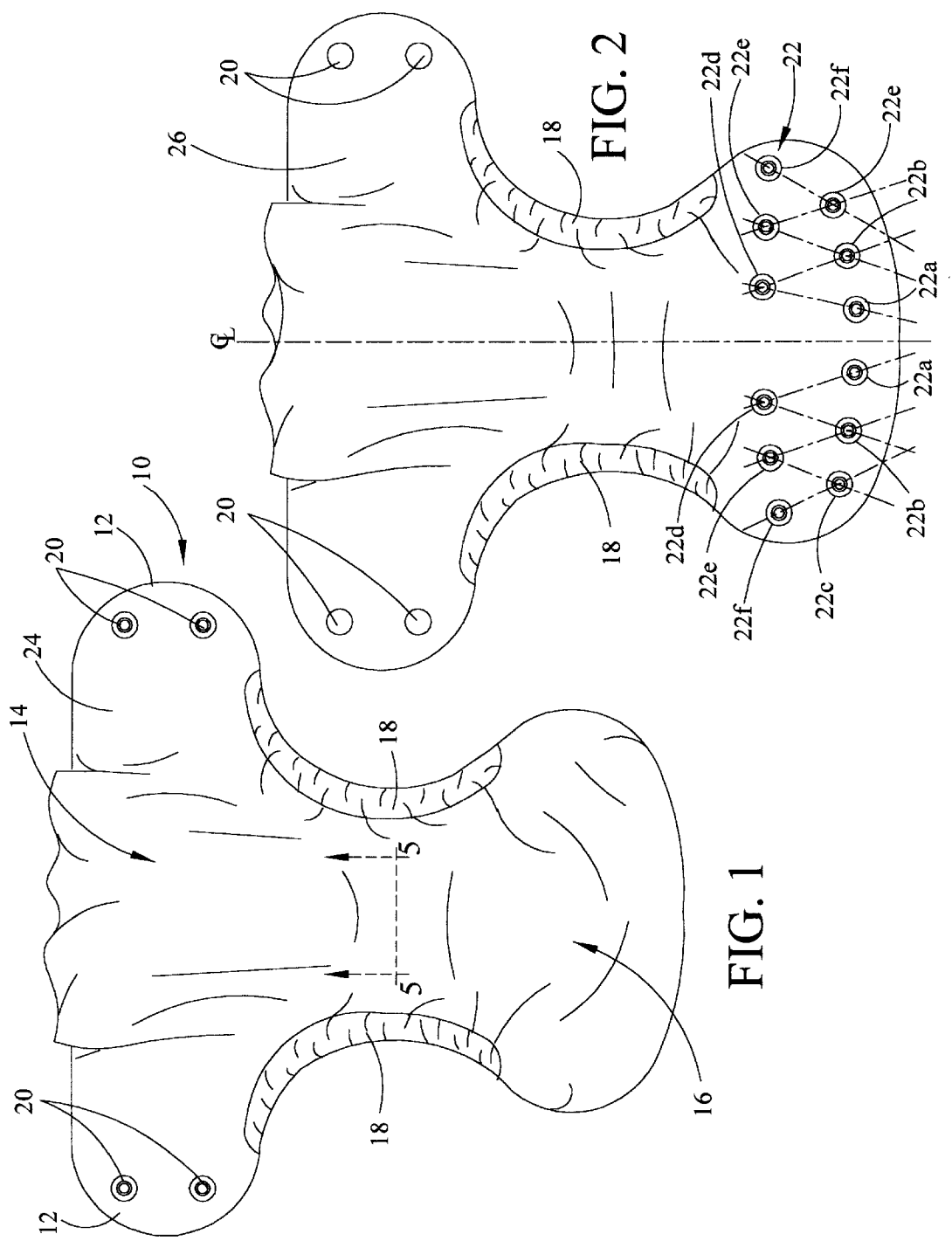

REUSABLE BABY DIAPER HAVING REUSABLE ABSORBENT INSERT

This application claims the benefit of Provisional application Ser. No. 60/218,785, filed Jul. 18, 2000.

BACKGROUND OF THE INVENTION

1. Field of the Invention

This invention relates generally to baby diapers and more particularly to the so-called reusable all-in-one diaper having multiple fabric layers with removable and washable cloth insert.

2. General Background

Parents now have the option of using a variety of diapers for their child, ranging from the conventional cloth diaper washed at home or provided by a laundry service, disposable diapers, or a combination of these types in an all-in-one diaper. Arguments are made on all sides regarding the health and sanitation issues, the energy and environmental cost, as well as the economics involved in using each type. However, case studies have clearly indicated that it all comes down to a personal choice based on the life style and economic advantages of the parent.

In cases where cloth diapering is the option of choice, frequent diaper changes are required to keep the child dry and thereby help reduce infections such as diaper rash. Cloth diapers absorb moisture but do not necessarily wick moisture away from the body. Cloth diapers become saturated very quickly; therefore, outer waterproof covers are often used to contain further spreading of the moisture. Such covers may simply be made of a disposable plastic or more elaborate laminates, such as knit polyester or cotton bonded to a urethane inner liner. Alternatively the so-called all-in-one diaper may be used that combines the diaper with a protective waterproof outer cover. Use of such covers or combinations often conceal the fact that the diaper is wet, as is also the case of disposable diapers. In addition such diapers may also include absorbent disposable liners made of multiple layers of cotton or reusable insert pads that are either sewn in place or allowed to float free between inner and outer liner laminates, A secondary issue focuses on the comfort of the baby with respect to the diaper applied. It is essential that the diaper be snug to insure retention and prevent leakage but not so tight as to be uncomfortable or hamper blood circulation in the child's legs due to elastic leg openings and not so tight as to create high humidity within the diaper.

Some studies even suggest the use of two diapers per changing to help insure dryness. Therefore, elastic covers or diapers with hook and loop fasteners that can cut and abrade the child and the addition of disposable multi-layers of absorbent material is clearly not the answer.

Further, book and loop fasteners generally only allow for waist adjustment and do nothing for the leg openings. Therefore, elastic is often used around the leg openings. This arrangement assumes that the waist and leg size are relative which is certainly not the case.

Obviously the key issues are to insure that the baby stays as dry as possible for as long as possible with the least bulk possible. The baby's comfort should be paramount and not dependent on convenience for the diaper changer.

SUMMARY OF THE INVENTION

According to the instant invention, there is provided an adjustable, form fitted, reusable diaper for infants that includes a reusable or disposable pad insertable between a soft permeable inner panel and an impermeable outer panel laminated with either a soft pile or a waterproof breathable or non-breathable elastomeric non-woven material. The diaper, having an hourglass configuration when open, is provided with expandable leg openings and waistband and fitted with hidden snap closures uniquely arranged to provide waist adjustment independently of leg opening adjustment and vise-versa. The diaper's use of a high pile permeable inner panel, such as polar fleece, wicks moisture away from the infant's body quickly where the washable, reusable pad located between the inner and outer panels absorbs it. The pad is then easily removed and replaced with a clean and dry pad, often without removal of the diaper from the infant.

BRIEF DESCRIPTION OF THE DRAWINGS

For a further understanding of the nature and objects of the present invention, reference should be made to the following detailed description taken in conjunction with the accompanying drawings, in which, like parts are given like reference numerals, and wherein:

FIG. 1 is an inside view of the preferred diaper embodiment;

FIG. 2 is and outside view of the preferred diaper embodiment;

DETAILED DESCRIPTION OF THE PREFERRED EMBODIMENT

Figure 4:
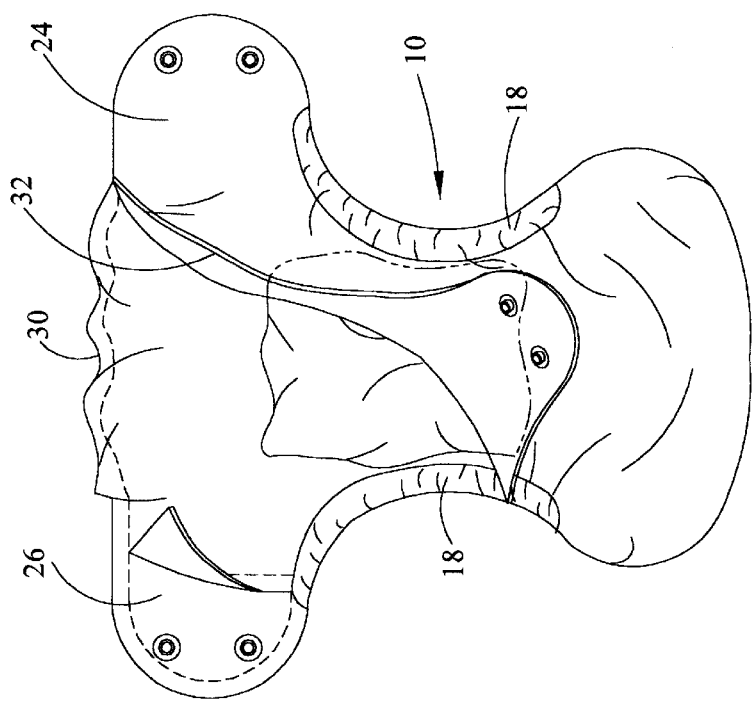
FIG. 4 is a peeled back view of the diaper layers.

The instant infant diaper invention 10, illustrated in FIG. 1 as viewed from the inside, is contoured in the classic hour glass shape having elongated wings 12 along the upper portion 14 which over lap the lower portion 16 when the diaper is folded in half, thereby forming waist closure and leg openings. The leg openings are lined with elastic sewn into the panel hem 18 to insure a snug fit Whiz around an infant's legs when folded. A pair of male plastic snaps 20, located vertically, are provided at each of the wing portions 12. Looking now at the outside of the diaper 10 as illustrated in FIG. 2, we see a dozen female plastic snap members 22 spaced and located in a cooperative manner with the male snaps 20, but in a unique manner. The male snap portions 20 penetrate both the inner panel 24 and the outer liner 26, whereas the female portion of the snap 22 only penetrates the outer panel 26. The female snap portions 22 are arranged so that each of 3 pairs of snaps are located at an acute angle of approximately 30 degrees off each side of the center longitudinal axis of the diaper 10. This unique snap arrangement allows the male snaps 20 to engage the female snaps 22 in any combination; for example, the uppermost male snaps 20 can engage either of the female snaps 22a, 22b or 22c, thereby adjusting the waist size of the diaper while the lower male snaps 20 may engage 22d, 22e, or 22f, thereby adjusting the leg openings. Other snap arrangements may also used to achieve the same result of allowing the waist to be adjusted without affecting the leg opening and vice versa. All such arrangements are considered as being within the scope of the invention.

Looking now at FIG. 4, we see the diaper 10 is a laminate composed of the inner panel 24 and the outer liner 26 sewn together peripherally, each panel being cut in a basic hour glass shape having upper and lower body portions 14,16 connected by a narrowing or restrictive intermediate or crotch portion 28. The upper body portion 14 is elongated or elliptically shaped to form wings 12 that define a manta ray configuration. The leading edge 32 of both the inner and outer panels are purposely not attached to each other in order to provide an aperture or mouth or opening into the space between the inner and outer panels 24,26.

Figure 5:
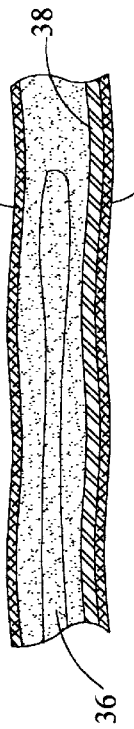
FIG. 5 is a partial cross section view taken along sight lines 5—5 in FIG. 1.
Figure 3:
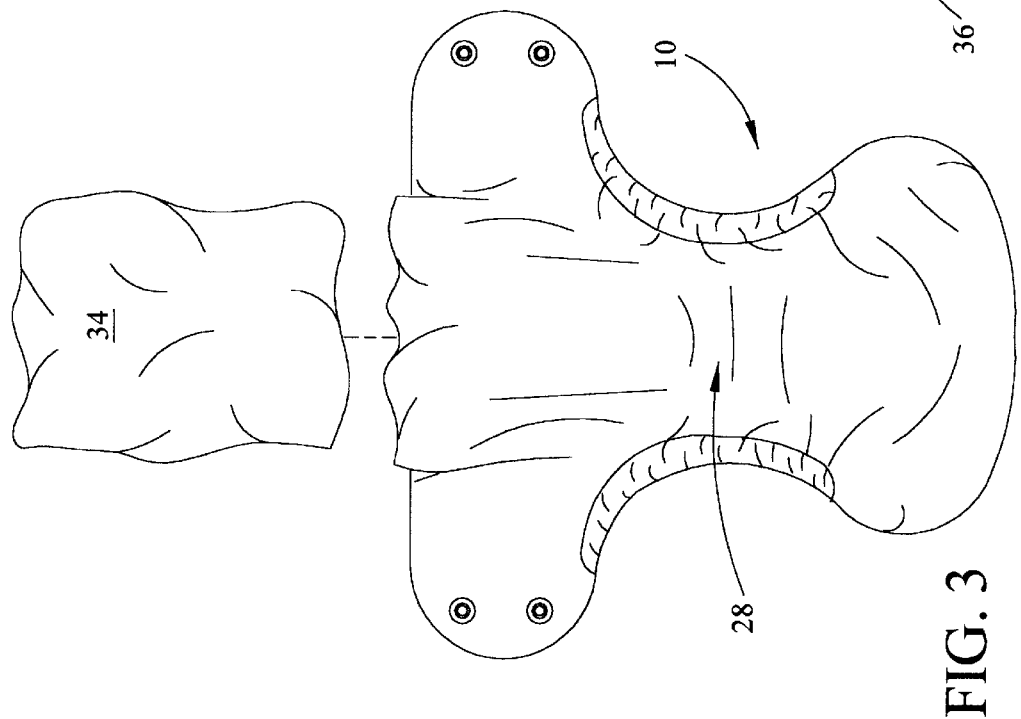
FIG. 3 is an exploded view of the preferred diaper embodiment with insert.

Hems 18 are provided for attaching elastic along the leg openings either side of the crotch portion 28 seen in FIG. 3. A hem 30 is also provided along the upper edge of the outer panel 26 to allow for waistline expansion and ease of insertion of the absorbent pad. A portion 32 of the upper edge of the inner panel 24, corresponding to the hem 30 along the upper edge of the outer panel 26, is purposely not sewn to the outer panel 26 to allow access to the space 36 seen in FIG. 5 between the inner and outer panels 24,26. An absorbent pad 34 as seen in FIG. 3 may be readily inserted between the inner and outer panels 24,26 and held firmly in the crotch area 28 by an infant's legs when wearing the diaper 10. The insert 34 may be a disposable pad or any absorbent, reusable material, such as one or more folded cotton cloth diapers.

The material used for the inner and outer panels 24,26 may be a spongy, high pile polyester knit material commonly referred to as Polar fleece. The non-absorbency of the synthetic fleece material rapidly wicks wetness away from the infant where it is absorbed by the insert 34. The fleece material's inability to retain moisture provides a dry barrier between the infant and the absorbent insert 34. The fleece material may be sprayed with a durable, water resistant chemical to help insure faster drying. Other pervious water resistant materials are anticipated, such as velour, sheep's wool fleece,and the like.

The outer panel 26 may be a leak-proof, expandable, polyurethane laminate 38 composed of breathable or non-breathable bonded polyester knit material coated with DRW, known in the art as durable water resistant chemical. Alternatively, the outer panel 26 may be a laminate composed of polar fleece 26 internally lined with the leak-proof, polyurethane laminate 38 composed of breathable or non-breathable bonded polyester knit material coated with DRW or a durable water resistant chemical.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in any limiting sense.

What is claimed is:

1. A reusable infant diaper comprising:
   a) inner and outer panels, each panel having upper and lower elliptical portions connected by an narrowing incurvate intermediate portion, said upper elliptical portions having a leading edge, each of said panels attached peripherally one to the other in matched contour;
   b) a first elastic strip attached to said inner and outer panels along each side of said intermediate portion;
   c) a second elastic strip attached along at least a portion of said leading edge of said outer panel;
   d) a first plurality of snap members attached to each end of both the inner and outer upper elliptical portions;
   e) a second plurality of snap members attached to said lower elliptical portion of said outer panel cooperatively fastenable with said first plurality of snap members; and
   f) a removable, reusable, absorbent pad inserted between said inner and outer panels and located along said intermediate portion.

2. The reusable infant diaper according to claim 1 wherein said inner and outer panels utilize a pervious material.

3. The reusable infant diaper according to claim 1 wherein an inner face of said outer panel is lined with an impervious material.

4. The reusable infant diaper according to claim 1 wherein said inner and outer panels are polar fleece.

5. The reusable infant diaper according to claim 1 wherein said outer panel is an expandable polyurethane laminate coated with a durable water resistant chemical.

6. The reusable infant diaper according to claim 1 wherein said second plurality of snap members are attached to said lower elliptical portion of said outer panel in a manner whereby said second plurality of snap members are arranged in pairs located at acute angles either side of a longitudinal center line running through said upper and lower elliptical portions.

7. The reusable infant diaper according to claim 1 wherein said second plurality of snap members are not attached to said inner panel.

8. A reusable infant diaper comprising:
   a) an inner and outer panel, each of said inner and outer panels having upper and lower body portions and a perimeter therearound;
   b) each of said inner and outer panels connecting said upper and lower body portions with a narrowing crotch portion;
   c) an elastic strip attached to each side of said crotch portion;
   d) a fastener attached to each of said upper and lower body portions; and
   e) said inner and outer panels being attached to one another around said perimeter except for along a leading edge, thereby forming an opening between said inner and outer panels such that a removable absorbent pad may be inserted between said inner and outer panels.

9. The reusable infant diaper according to claim 8, wherein said inner panel is a pervious material.

10. The reusable infant diaper according to claim 9, wherein said inner panel is formed of polar fleece.

11. The reusable infant diaper according to claim 8, wherein said outer panel is impervious.

12. The reusable infant diaper according to claim 8, wherein an absorbent pad is positioned between said inner and outer panels.

13. The reusable infant diaper according to claim 8, wherein said fasteners are snap members.

* * * * *